(12) United States Patent
Ponsi et al.

(10) Patent No.: US 7,798,984 B2
(45) Date of Patent: Sep. 21, 2010

(54) HEEL ULCER PREVENTION AND CUSHIONING BOOT

(75) Inventors: Lawrence G. Ponsi, Wheeling, IL (US); Barbara T. Skiba, Chicago, IL (US); Steven Brown, Crystal Lake, IL (US)

(73) Assignee: Sage Products, Inc., Cary, IL (US)

( * ) Notice: Subject to any disclaimer, the term of this patent is extended or adjusted under 35 U.S.C. 154(b) by 1311 days.

(21) Appl. No.: 11/240,679

(22) Filed: Sep. 30, 2005

(65) Prior Publication Data

US 2007/0074427 A1    Apr. 5, 2007

(51) Int. Cl.
*A61F 5/00* (2006.01)

(52) U.S. Cl. .............................. 602/61; 602/23; 128/882

(58) Field of Classification Search .................. 602/23, 602/60–65, 27; 128/882; 36/88–90; 5/649–651
See application file for complete search history.

(56) References Cited

U.S. PATENT DOCUMENTS

| | | | |
|---|---|---|---|
| 4,186,738 A | 2/1980 | Schleicher | |
| 5,050,620 A | 9/1991 | Cooper | |
| 5,052,128 A | 10/1991 | Lonardo | |
| 5,078,128 A | 1/1992 | Grim | |
| 5,226,245 A * | 7/1993 | Lamont | 36/9 R |
| 5,464,385 A | 11/1995 | Grim | |
| 5,472,414 A | 12/1995 | Detty | |
| 5,827,211 A * | 10/1998 | Sellinger | 602/27 |
| 5,853,380 A | 12/1998 | Miller | |
| 5,876,364 A * | 3/1999 | Herbst | 602/27 |
| 6,056,713 A * | 5/2000 | Hayashi | 602/27 |
| 6,126,627 A | 10/2000 | Brennan | |
| 6,640,810 B1 | 11/2003 | Callsen | |

* cited by examiner

*Primary Examiner*—Kim M Lewis
(74) *Attorney, Agent, or Firm*—Barnes & Thornburg LLP

(57) ABSTRACT

A cushioning boot for bed-ridden patients. The boot includes a thickly-padded leg engaging portion and foot engaging portion with a front opening for easy insertion of a patient foot and leg. A series of stretchable, adjustable closure panels are removably secured to the boot for positioning and inserted leg in the proper orientation and retaining it in place.

15 Claims, 17 Drawing Sheets

HEEL ULCER PREVENTION AND CUSHIONING BOOT

BACKGROUND OF THE INVENTION

This invention relates to patient care, and in particular to a cushioning boot for the comfort and protection of a bedridden patient.

Boot-like structures have been developed for protecting a patient who is bedridden for any number of reasons. The boots provide heel support and comfort, as well as proper positioning of the patient's leg to avoid creating other problems, such as ulcers, for a patient that must remain bedridden for a long period of time. Such structures are disclosed in U.S. Pat. Nos. 4,186,738; 5,226,245; 5,853,380; 5,876,364 and 6,640,810, for example. Such devices, while better than nothing at all, still have not solved the problem of creation of other problems for patients who are bedridden.

Other boot-like devices have been developed for strengthening or protecting a person's foot and leg. Examples of such devices are found in U.S. Pat. Nos. 5,078,128, 5,464,385, 6,126,627, 5,472,414 and 5,050,620. A similar device, when used to help transporting of an invalid patient, is set forth in U.S. Pat. No. 5,052,128.

The present invention is directed to an improved cushioning boot, used primarily with patients who are bedridden for an extended period of time. The invention provides comfort and extended wear unavailable in the prior art.

SUMMARY OF THE INVENTION

The invention is directed to a cushioning boot, comprising a leg engaging portion and a foot engaging portion, with the portions being padded and having a leg-accepting aperture extending along a front side of the boot. An adjustable closure panel is removably secured to the boot, a first portion of the panel extending substantially along the leg engaging portion and a second portion of the panel extending along a part of the foot engaging portion.

In accordance with one form of the invention, at least the leg engaging portion has an exterior surface having a low coefficient of friction and an interior surface having a high coefficient of friction. A leg seated within the foot cushioning boot is therefore held properly in place, but allowed to move with the boot along bed linens or on wherever else the boot is being used.

Preferably, a third stretchable, adjustable closure panel is provided, extending between and at least partially overlapping the first and second closure panel portions. The third closure panel provides increased force at critically desired areas.

Preferably, the panels are made substantially of stretchable fabric or material, such as spandex. Also, the first panel portion includes a view port for viewing parts of the patient's leg without removing the closure panel. In all forms of the invention, it is preferred that the closure panels are secured to one another, and a tether may be provided for securing the panels to the foot cushioning boot.

Means is provided for orienting the closure panels for securing the panels to the boot. Preferably, this comprises fasteners for securing each of the panels to the boot, with each fastener including a first fastening portion on one of the panels and a second fastening portion on the boot. Hook and loop fasteners are the preferred form to provide adequate adjustability. Also, for orienting, the fastening portions can be color coded to aid the user.

In another form of the invention, the cushioning boot comprises a leg engaging portion and a foot engaging portion, with a leg-accepting aperture extending along a front side of the boot. The leg engaging portion comprises a leg orienting section and a leg cushioning section, with the leg cushioning section being positioned toward the leg-accepting aperture and at least partially extending over the leg orienting section.

In this form of the invention, the leg orienting section comprises a pair of elongated, padded tubes extending substantially from a heel aperture proximate the foot engaging portion to a distal leg opening. The leg cushioning section comprises a padding which overlies the tubes. The foot engaging portion is also padded and includes a foot orientation section. The foot orientation section comprises a furrow extending longitudinally in the foot engaging portion.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
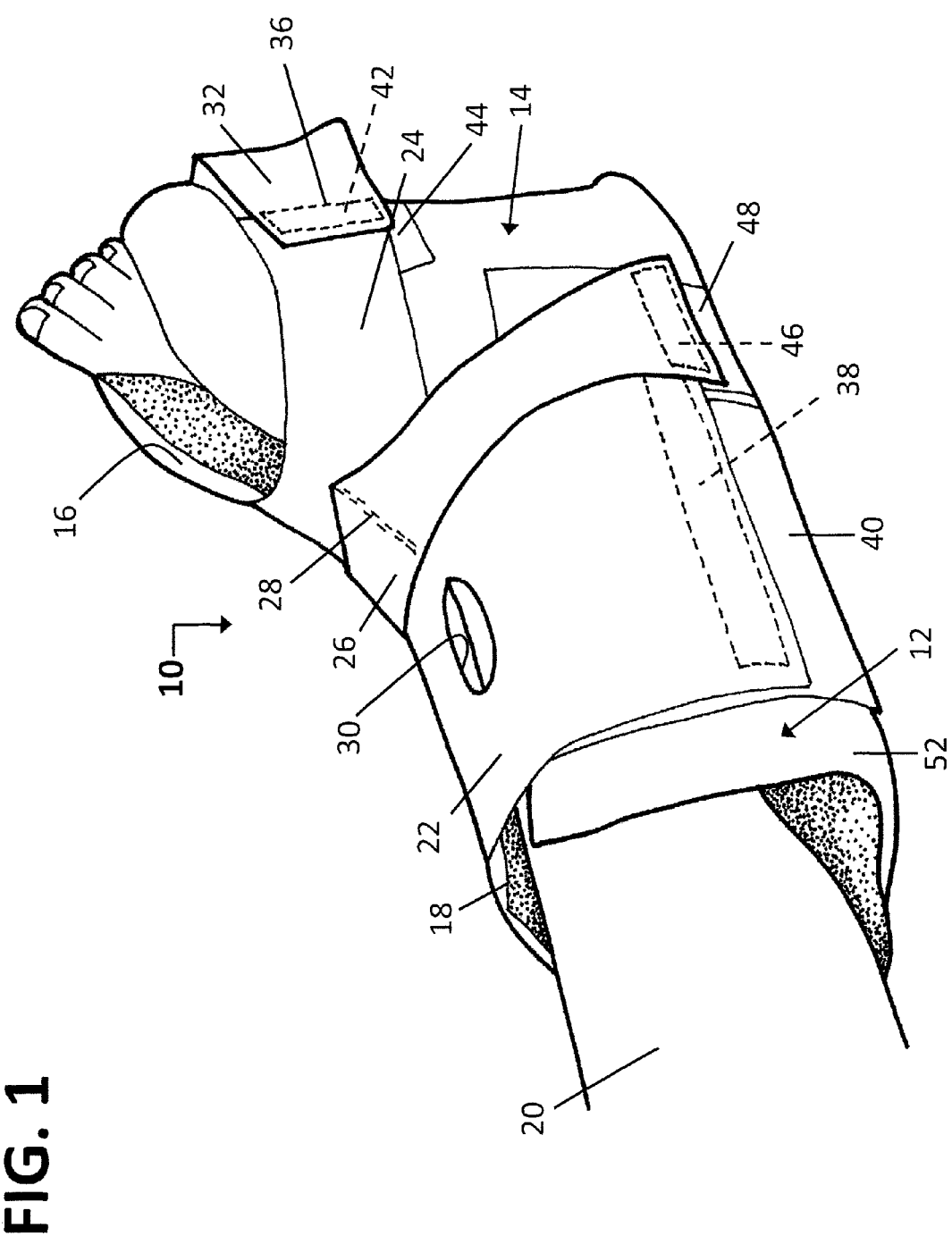
FIG. 1 is a prospective view of a cushioning boot according to the invention, when installed on a patient's leg.
Figure 2:
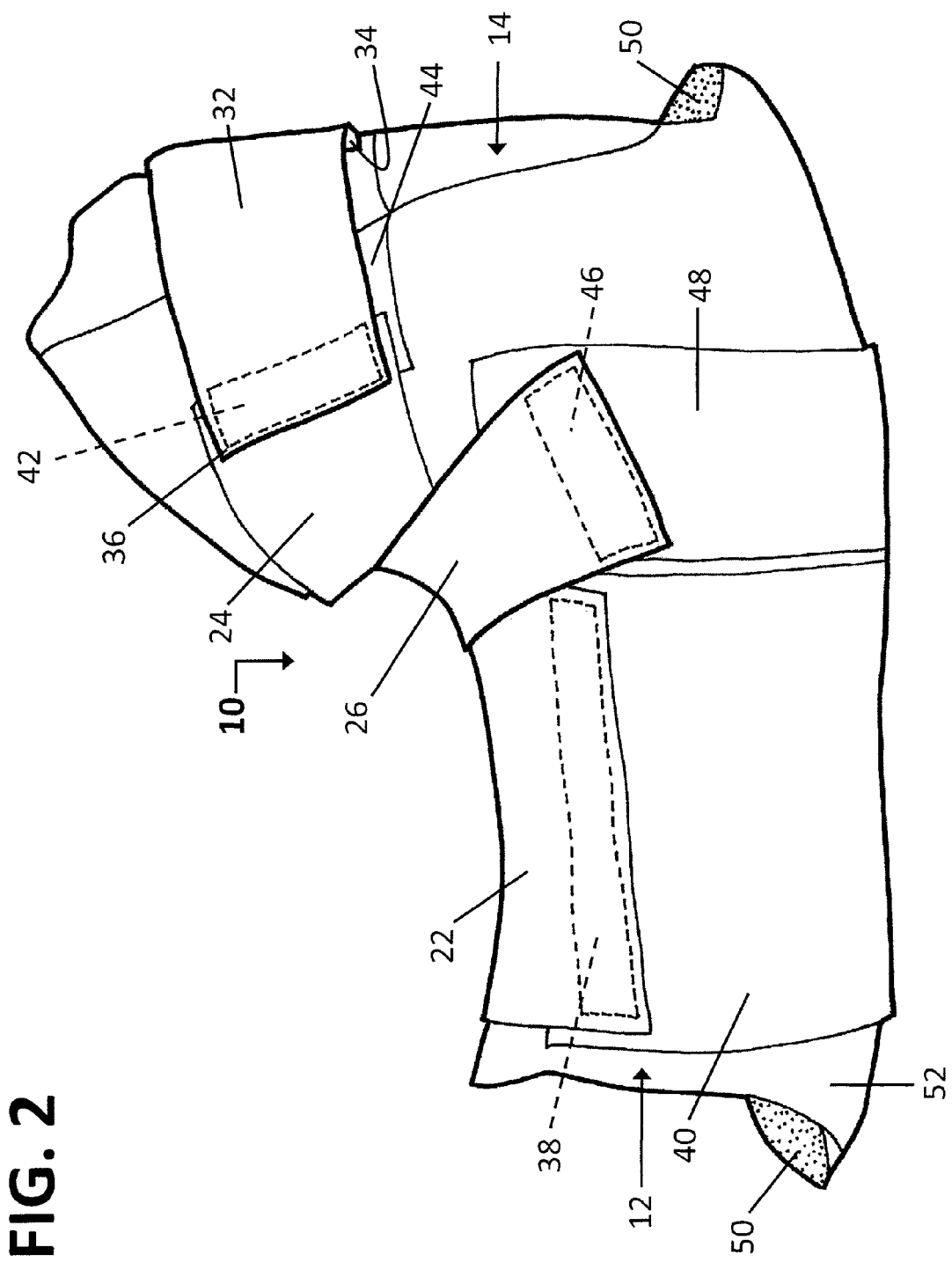
FIG. 2 is a side elevational view of one side of the cushioning boot according to the invention, with closures in place.
Figure 3:
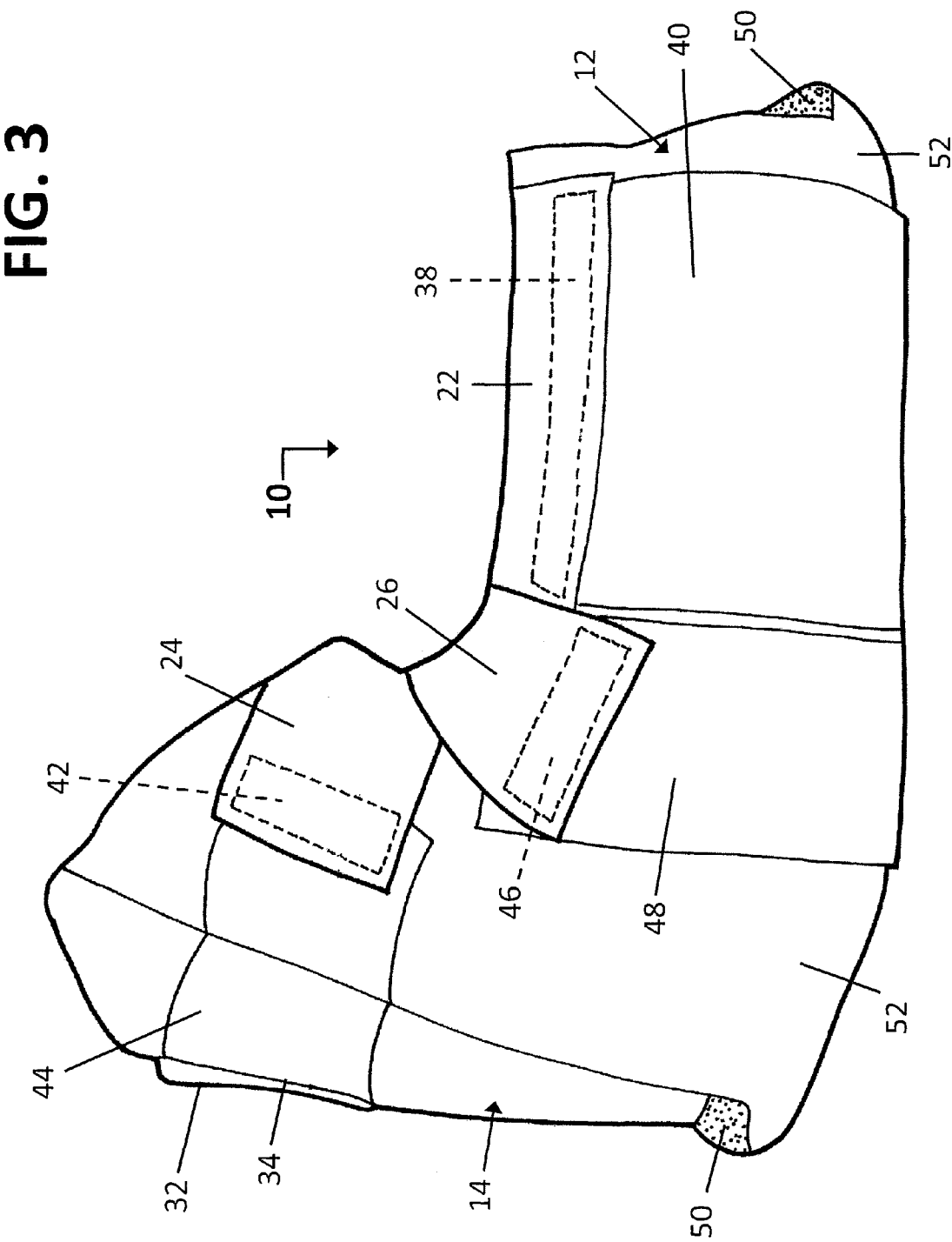
FIG. 3 is a view similar to FIG. 2 of the opposite side of the cushioning boot.

A first form of a cushioning boot according to the invention is shown generally at 10 in drawing FIGS. 1-6. The cushioning boot comprises two sections, a leg engaging portion 12 and a foot engaging portion 14 which are generally a unitary structure being thickly padded at 16 and having a leg-accepting aperture 18 extending along the front of the cushioning boot 10. The padding 16 can be any material, but preferably is as pillow-like as possible to replicate the feel of typical hospital pillows which are regularly used for supporting a patient's foot.

For maintaining a leg 20 in the cushioning boot 10 as shown in FIG. 1, the boot 10 also includes a panel comprising at least two stretchable, adjustable closure panel portions removably secured to the boot 10. A first panel portion 22 extends substantially along the leg engaging portion 12, and a second panel portion 24 extends along the portion of the foot engaging portion 14. A third stretchable, adjustable closure panel 26 is also included, extending between and at least partially overlapping the first and second closure panel portions 22 and 24. Preferably, the first and second closure panel portions 22 and 24 are a continuous piece of material cut to shape, and the third closure panel 26 is a section of similar material which is joined, at stitching 28, to an area between the first closure panel 22 and the second closure panel 24. Other means of attachment of the third panel 26 will be evident to one skilled in the art.

The panels 22 through 26 are, as their names suggest, panels rather than typical straps, and are both stretchable due to the nature of the material used, and adjustable due to the nature of their closures, described below. Preferably, the panels are made wholly or substantially of spandex, which is a textile filament fiber in which the fiber forming substance is a long-chain synthetic polymer comprised of at least 85% of a segmented polyurethane. Other materials similar to spandex can be employed, although spandex has been found to be the preferred material to perform as desired.

To allow inspection of patient's leg without opening the first panel 22, the first panel portion 22 includes a view port 30 as illustrated. The view port 30 is simply an area where a section of the material of the first panel portion 22 has been removed.

As described in greater detail below, the panels 22 through 28 are fully removable from the cushioning boot 10. So as to not be inadvertently lost when removed, it is preferred that a tether 32 be included, in the form of the invention illustrated being simply a strap that is permanently affixed to the foot engaging portion 14 at 34 and which is stitched at 36 to the second panel 24. The material of the tether 32 is unimportant so long that it is sufficiently robust to secure the combination of the first through third panels 22 through 28 permanently to the boot 10. Obviously, it is not mandatory that a tether be used.

As indicated above, the closure panels 22 through 28 are adjustable and removably secured to the boot 10. That is by means of fasteners with each of the panels 22 through 28 being removably secured at its opposite ends to the boot 10. Preferably, hook and loop fasteners are employed, with the hook portion preferably secured to the underside of each end of each of the panels 22 through 26, and the loop portion being sewn or otherwise affixed on appropriate exterior locations of the boot 10. Thus, as illustrated in drawing figures, the first panel portion 22, at its opposite ends, has elongated fastener hook portions 38 stitched thereto, and large fastener loop segments 40 secured to opposite sides of the outside of the leg engaging portion 12. Similarly, the opposite ends of the second panel portion 24 have a fastener hook portion 42 secured to the underside thereof which engage fastener loop segments 44 secured to the foot engaging portion 14. Finally, the opposite ends of the third panel 26 include fastener hook portions 46 stitched on the underside thereof which engage fastener loop segments 48 secured to the leg engaging portion 12. The hook and loop portions can be the well-known Velcro fastener, or other similar structures. Other types of fasteners can be used, as well, although hook and loop fasteners provide substantial versatility by permitting incorporation of large loop segments 40, 44 and 48 which permit significant adjustment of the panels 22 through 26 for proper tension and orientation.

To also aid in proper placement of the panels 22 through 26, the panels can be provided with appropriate means for orienting them. For example, the panels portions 22 and 24 can be fabricated in one color, and secured to portions of the boot 12 having like-colored loop segments, while the third panel 26 can be fabricated of a different color, and secured to a loop segment of the same different color. Alternatively, the ends of the panels 22 through 26 having the hook portions 38, 42 and 46 can be color-coded, and the receiving respective loop segments 40, 44 and 48 can be similarly color-coded. Alternatively still, the panels and loop segments can be numbered, lettered or otherwise identified for proper attachment and orientation, as will be apparent to one skilled in the art.

It is important that the patient's leg 20 be properly oriented and retained in the cushioning boot 10. At the same time, it is preferable that the foot cushioning boot 10, with the leg 20 therein, be readily movable by the doctor or patient, when desired. To that end, the cushioning boot 10, at least in the leg engaging portion 12, has an interior surface 50 with a high coefficient of friction, while having an exterior surface 52 with a low coefficient friction. The interior surface 50 can be rubber-like and made of any material that is relatively "grippy", so that when the leg 20 is properly installed within the cushioning boot 10 and the panels 22 through 26 stretched and closed, the leg 20 is held firmly yet comfortably in place. The exterior surface 52, on the other hand, is relatively slippery, and can be a plastic material such as polyester or any other material that does have a coefficient of friction low enough so that the boot 10, when worn, can be easily slid along bed clothing or any other surface upon which the boot 10 rests.

One form of the inner surface 50 may be a warp knit tricot material. Preferably, the material is brushed, napped or sanded to raise its pile for comfort. For greater utility of the boot 10, the tricot can be treated, before raising of its pile, with a water repellant, such as a PTFE or other commercially available treatment to improve water repellency. Then, to give the inner surface 50 a high co-efficient of friction, an additional material, such as a hot melt adhesive or appropriate plastic, can be applied as a discontinuous coating, thus promoting breatheability of the inner surface 50. Other means of forming a relatively grippy inner surface can be employed, as well and still fall within the scope of the invention.

Figure 4:
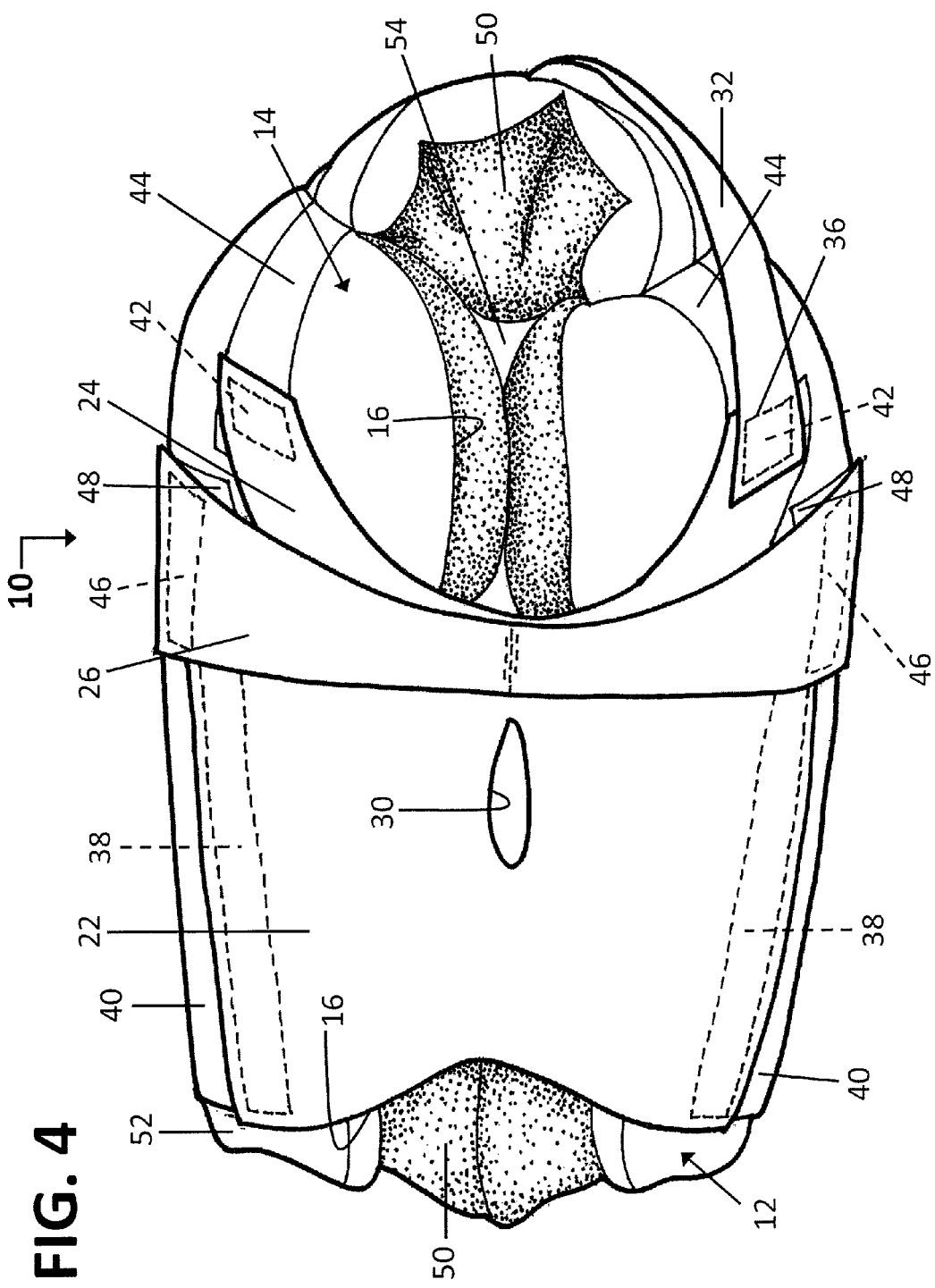
FIG. 4 is a front elevational view of the cushioning boot, with the closures in place.
Figure 5:
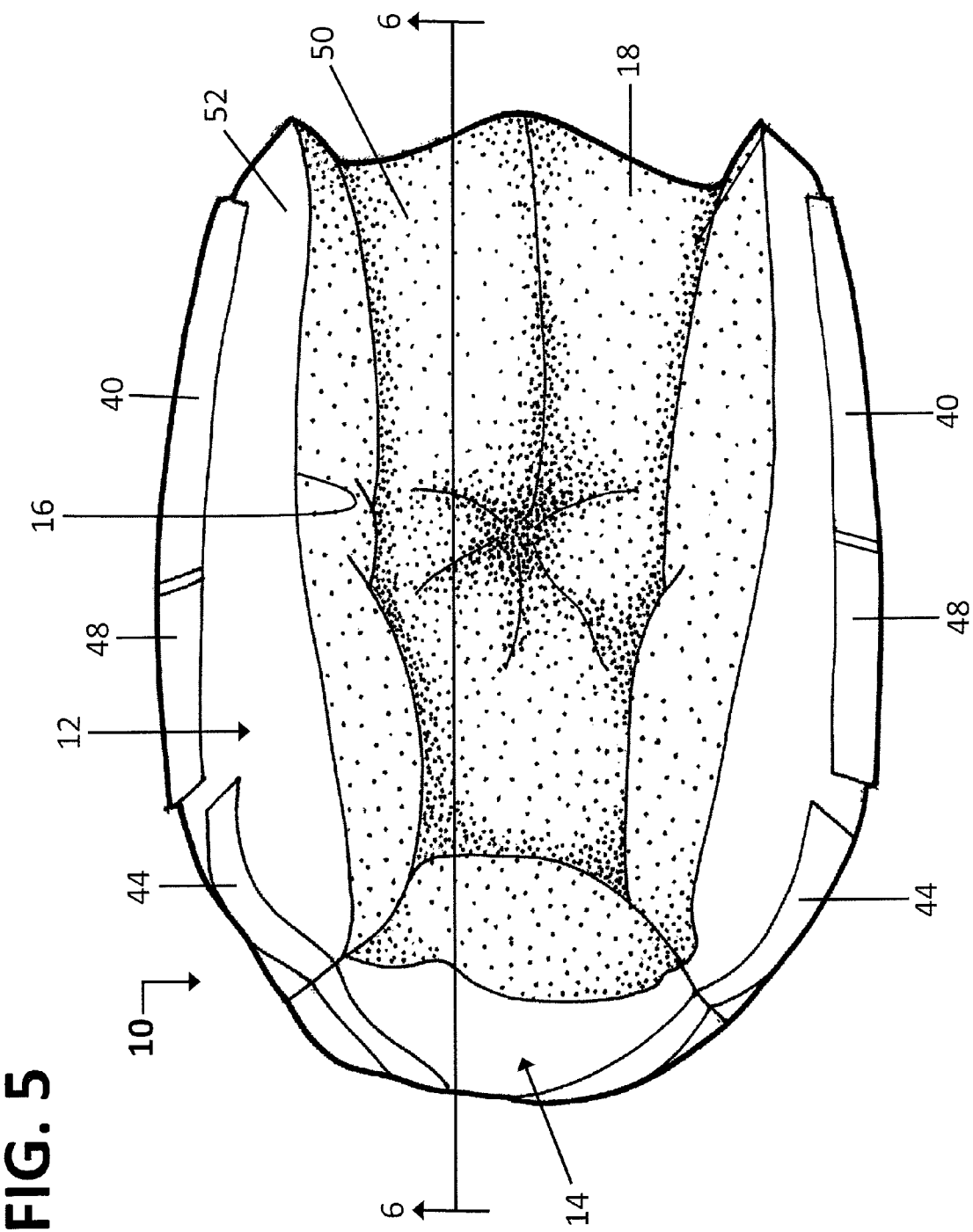
FIG. 5 is a top plan view of the cushioning boot, with the closures removed to illustrate detail.
Figure 6:
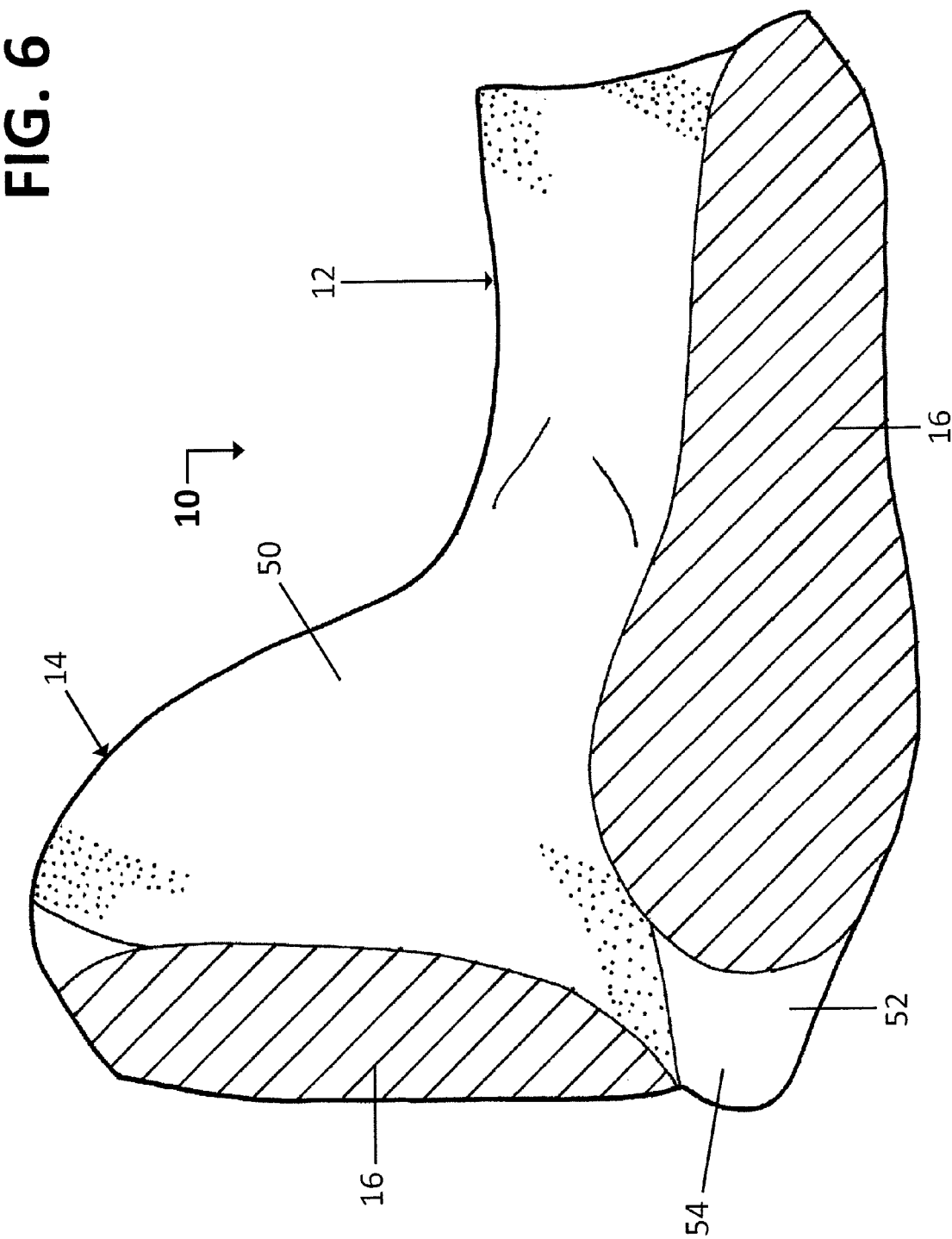
FIG. 6 is cross sectional illustration taken along lines 6-6 of FIG. 5.

It is preferred that the boot 10 have an open heel, where the leg engaging portion 12 and the foot engaging portion merge into one another. An appropriate aperture 54 is best shown in FIG. 4.

A second form of a cushioning boot according to the invention is shown generally at 10' in FIGS. 7 through 14. Those elements of the cushioning boot 10' that are identical to the first form of FIGS. 1 through 6 bear the same reference numerals, and those elements that vary in some manner from what is shown in FIGS. 1 through 6 bear primed reference numerals. The various elements, to the extent that they are the same, will therefore not be described in greater detail and reference is made to the above description of the embodiment of FIGS. 1 through 6 for greater detail.

There are two primary differences between the cushioning boot 10' of FIGS. 7 through 14 and the cushioning boot 10 of FIGS. 1 through 6. Those two differences are the construction of the leg engaging portion 12' and the construction of the foot engaging portion 14'.

Figure 13:
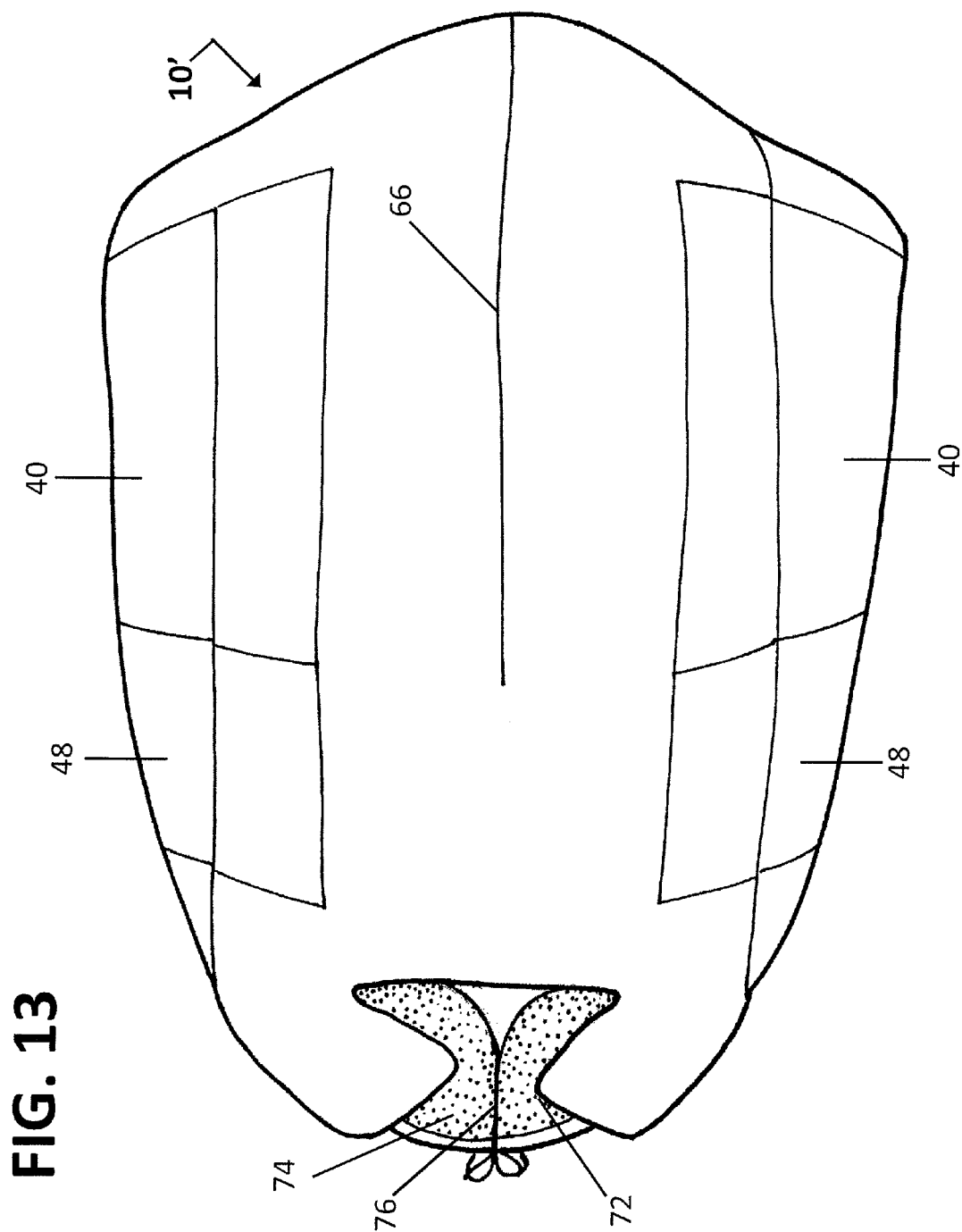
FIG. 13 is a rear elevational view of the cushioning boot of FIG. 7, but with the closures removed to illustrate detail.

The leg engaging portion 12' is composed of two parts, a first padded portion 60 and a second padded portion 62, as best shown in FIGS. 9 through 12. The first padded portion 60 is "beneath" the second padded portion 62 in relation to a person wearing the cushioning boot 10', and the first padded portion 60 includes an internal padding 64, and is formed into two tube-like portions by means of a stitching 66 or other similar means of separating and gathering the internal padding 64. The stitching 66, as best shown in FIG. 13, preferably extends over half of the length of the leg engaging portion 12', and can extend substantially more. It is preferred, however, that where a wearer's Achilles Tendon is located, the stitching 66 be absent for appropriate support of the Achilles Tendon. The padding 64 can be any material, and is preferably a bit more dense than the padding of the second padded portion 62 described below. Side portions of the leg engaging portion 12' also have internal padding 64, as in the first form of the invention.

The first padded portion 60 is overlain by the second padded portion 62, and the second padded portion 62 includes an internal padding 68. The padding of the internal padded portion 68 can be any material, and is preferably a bit less dense than that of the internal padding 64 so that it is as pillow-like as possible to replicate the feel of typical hospital pillows which are regularly used for supporting a patient's foot. The internal padding 64, however, is more dense, so that when a patient's leg is captured within the cushioning boot 10', the tubular nature of the first padded portion 60 tends to guide and seat the leg properly within the cushioning boot 10', while the leg is appropriately supported and protected by the second padded portion 62.

Figure 7:
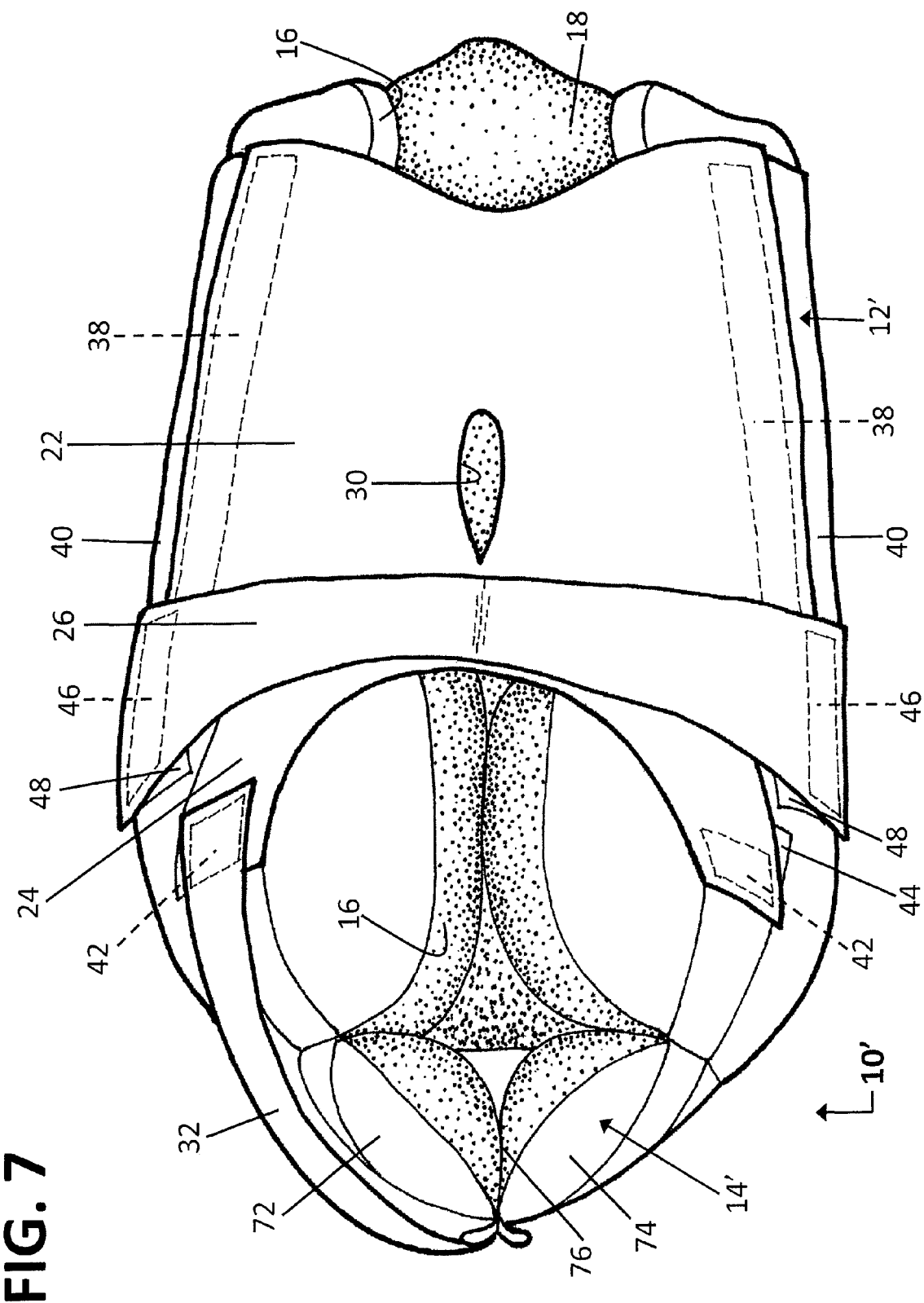
FIG. 7 is a front elevational view of a second embodiment of the cushioning boot, similar to FIG. 4, with the closures in place.
Figure 8:
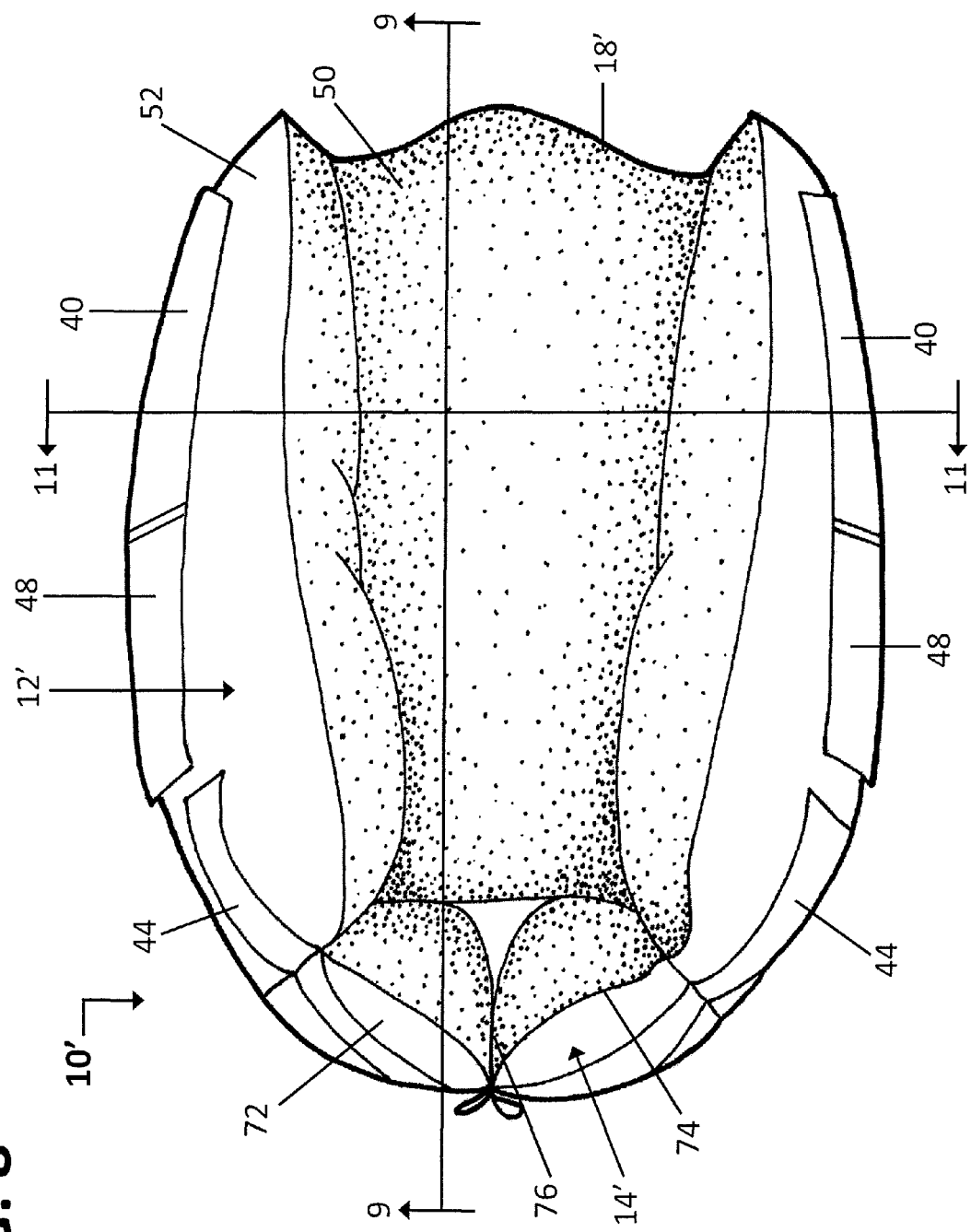
FIG. 8 is a top plan view of the cushioning boot of FIG. 7, with the closures removed to illustrate details.
Figure 9:
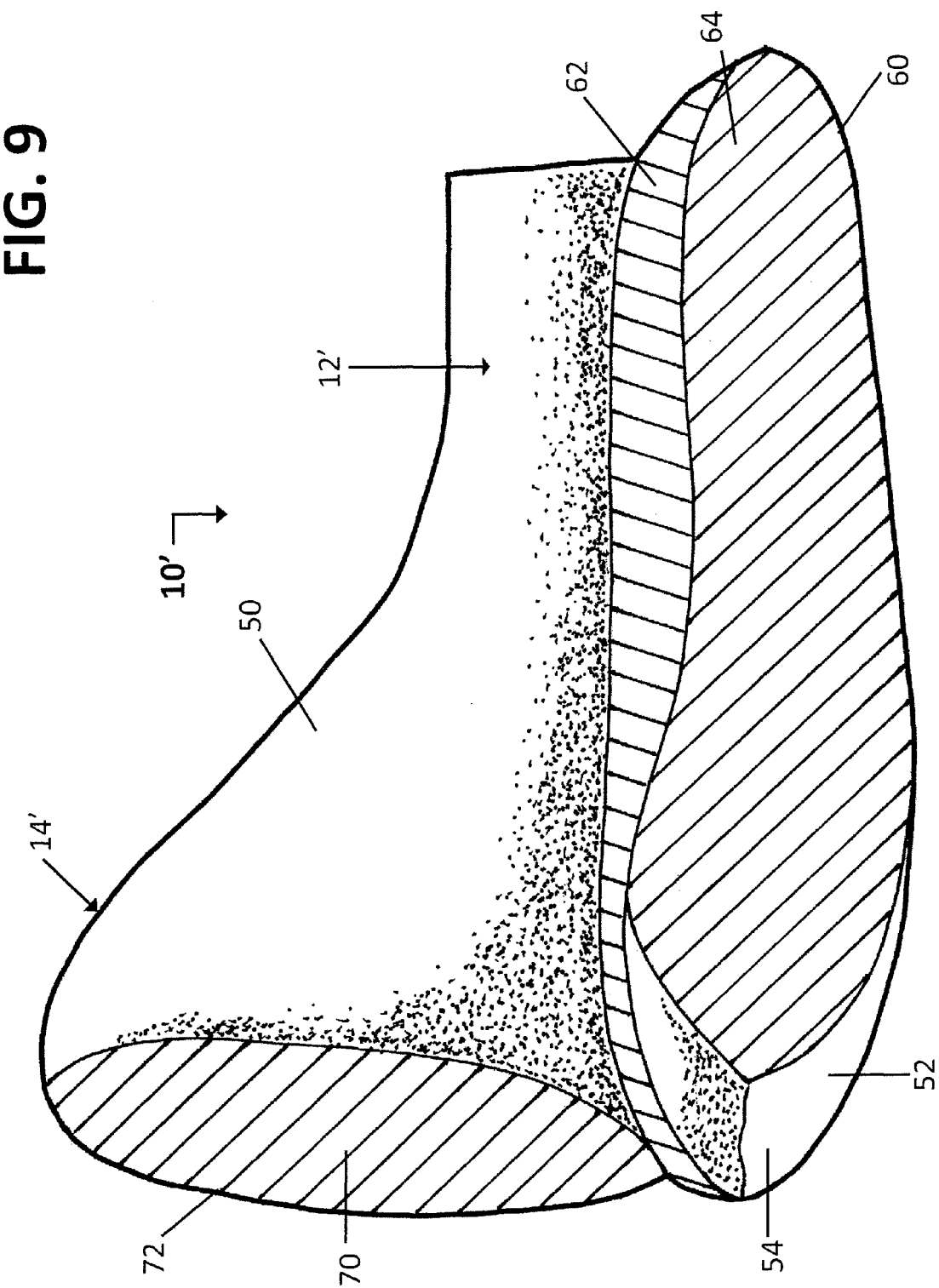
FIG. 9 is a cross sectional illustration taken along lines 9-9 of FIG. 8.
Figure 10:
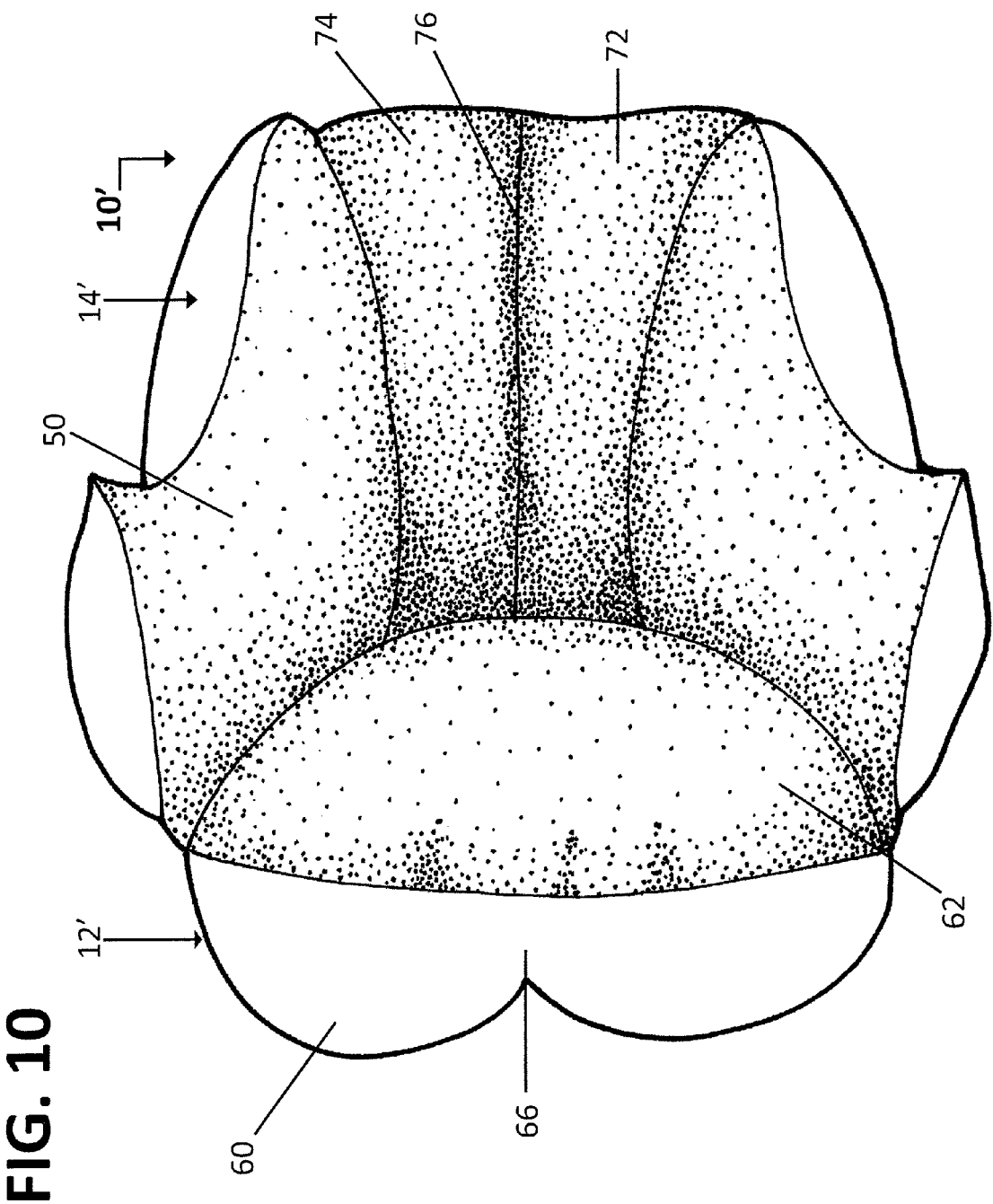
FIG. 10 is an elevational end view of the cushioning boot of the second embodiment of the invention, taken from the right end of FIG. 8.
Figure 11:
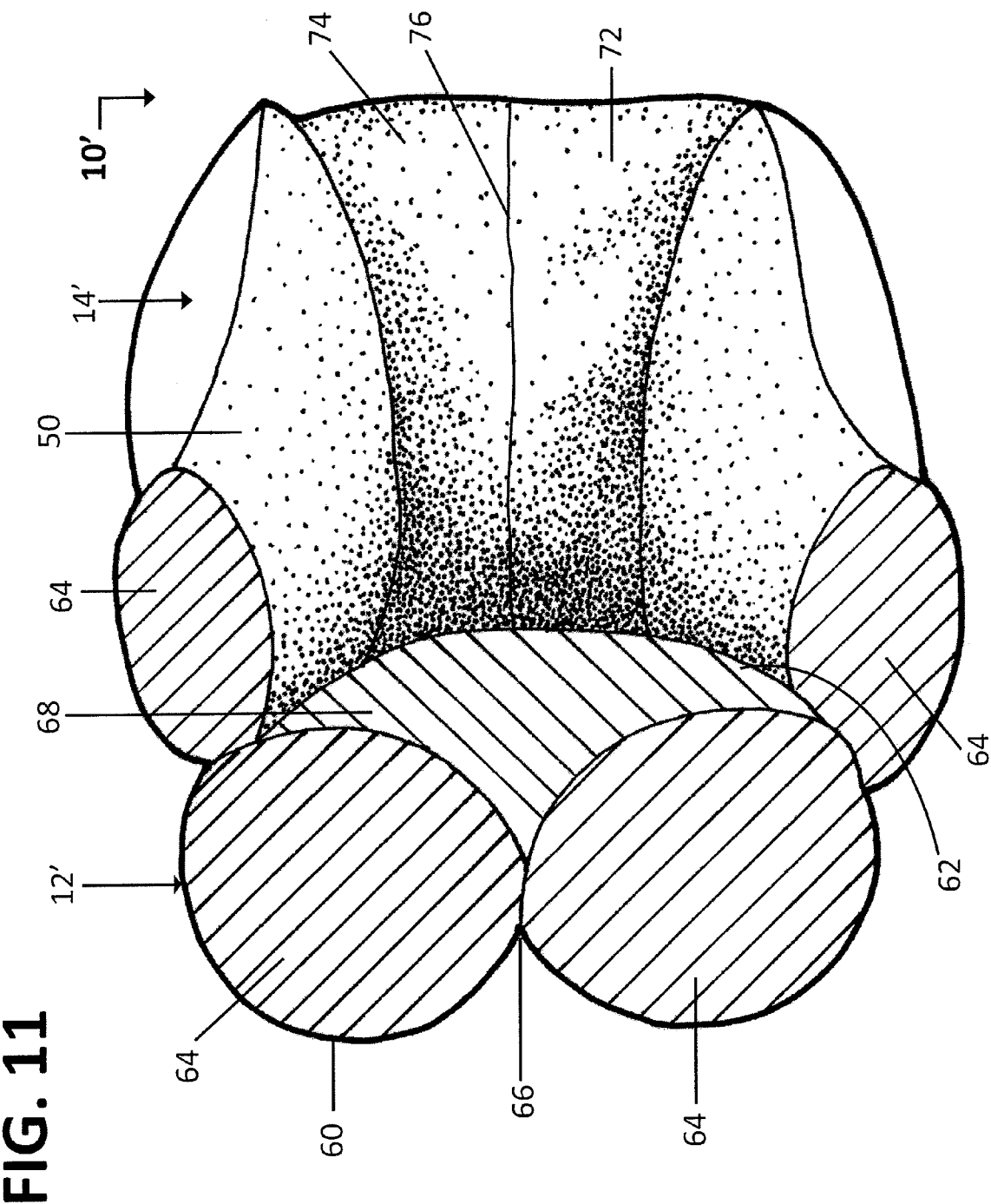
FIG. 11 is a cross sectional view taken along lines 11-11 of FIG. 8.
Figure 12:
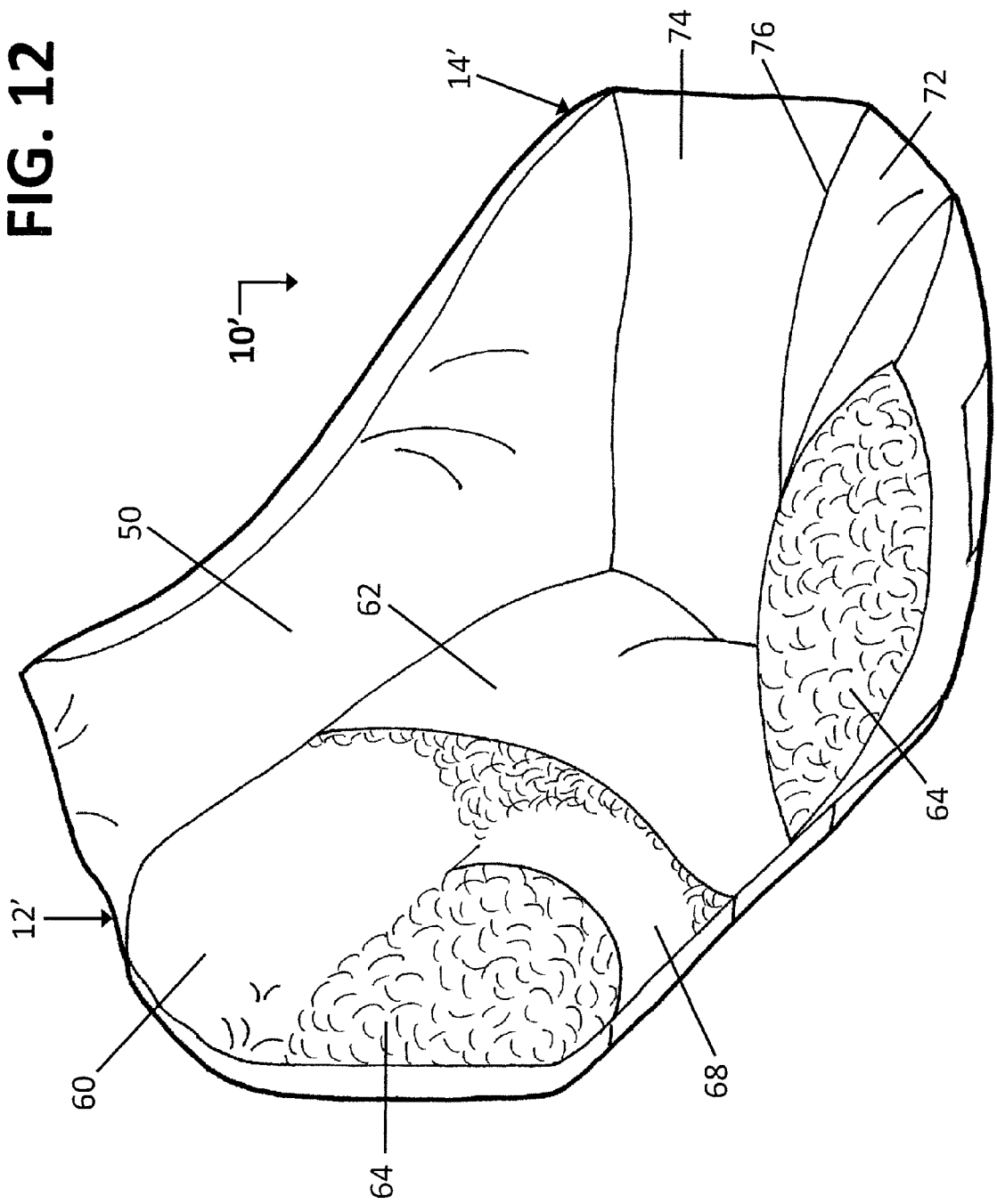
FIG. 12 is an oblique partial cross section of the second embodiment of the cushioning boot illustrated in FIG. 7.

The foot engaging portion 14' of the second embodiment of the invention is padded with an internal padding 70 similar to the first embodiment of the invention, except that the padding 70 is gathered into two tubular-like portions 72 and 74 as best shown in FIG. 7 and 8. A stitching 76, or any other means of gathering the internal padding 70 into the tubular portions 72 and 74, also helps seat and orient the cushioning boot 10' when worn. The foot naturally tends to "center" in the foot engaging portion 14' due to its center stitching.

Figure 14:
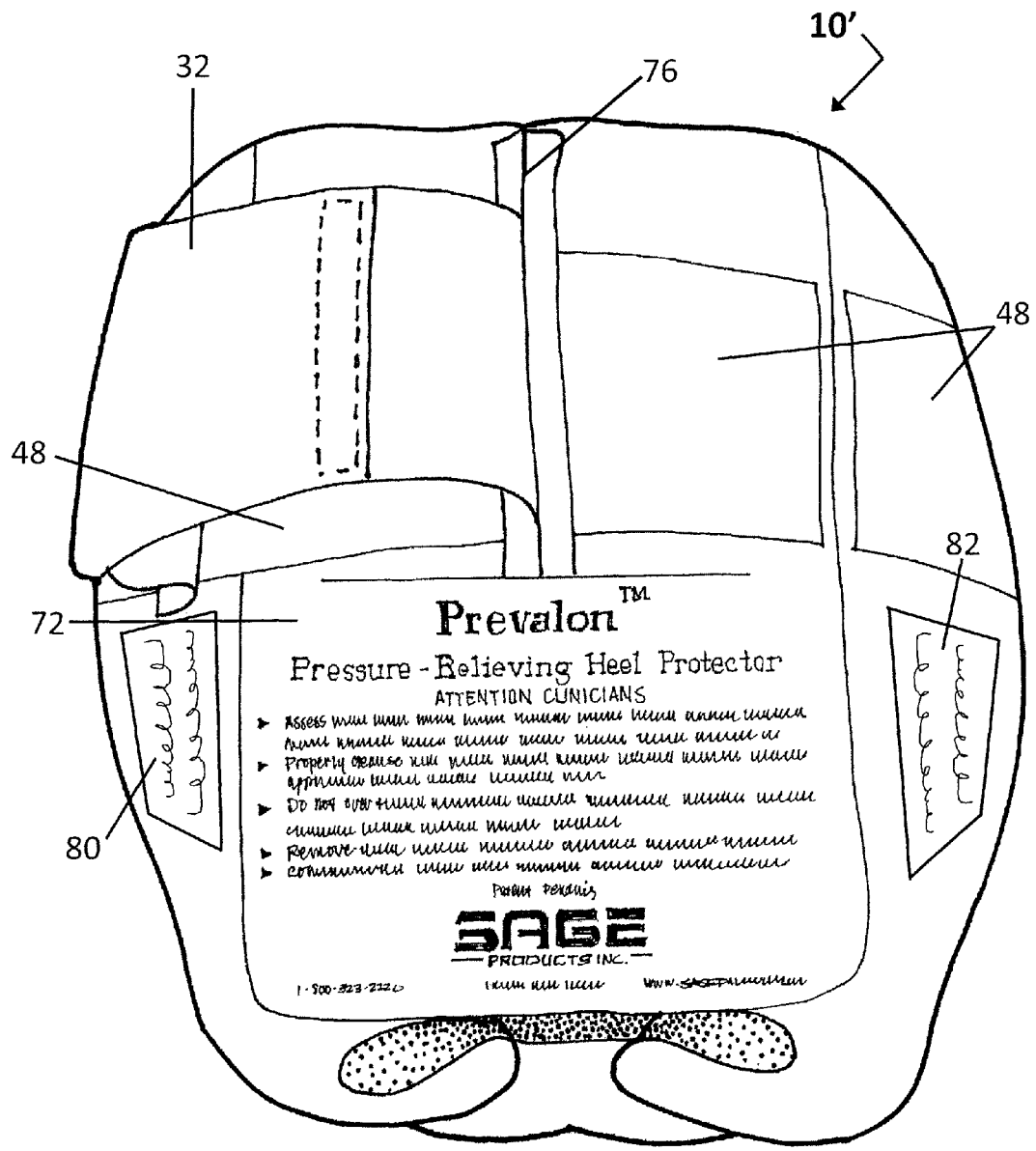
FIG. 14 is an end elevational illustration of the cushioning boot taken from the right of FIG. 7.

A label or labels can be applied to the cushioning boot 10 to provide appropriate information. As shown in FIG. 14, a label 78 can be applied to the bottom to appropriately identify the cushioning boot 10 and its use. Alternatively, the label 78 can be replaced or supplemented by opposite labels 80 and 82, with the label 80 having identification information such as manufacturer, etc., and the label 82 being instructional, providing information concerning use of the cushioning boot 10.

Figure 15:
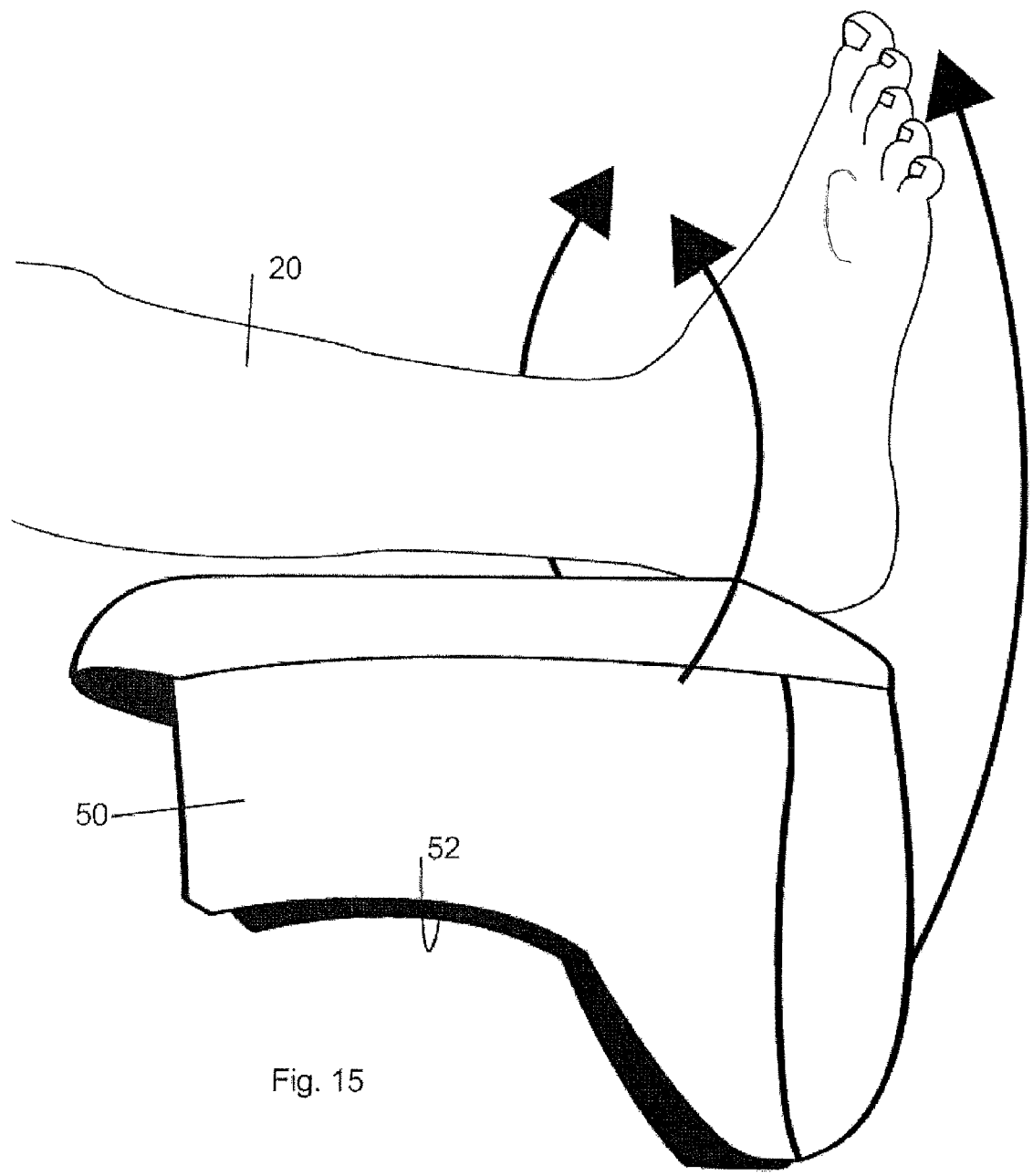
FIG. 15 is an elevational illustration of the cushioning boot, inside out, as it is being attached to a leg.
Figure 16:
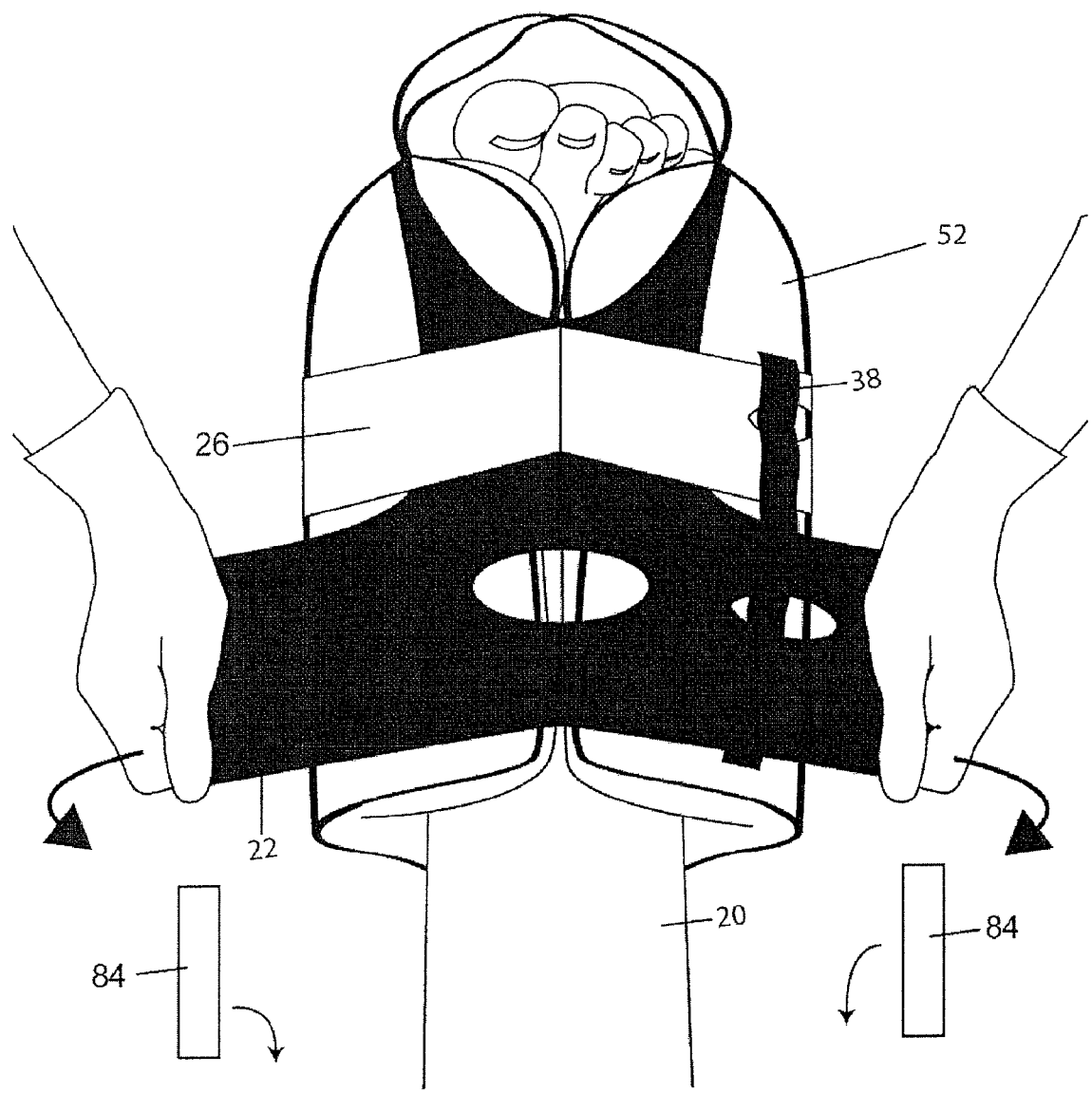
FIG. 16 is a top plan view of donning of the cushioning boot of FIG. 15.
Figure 17:
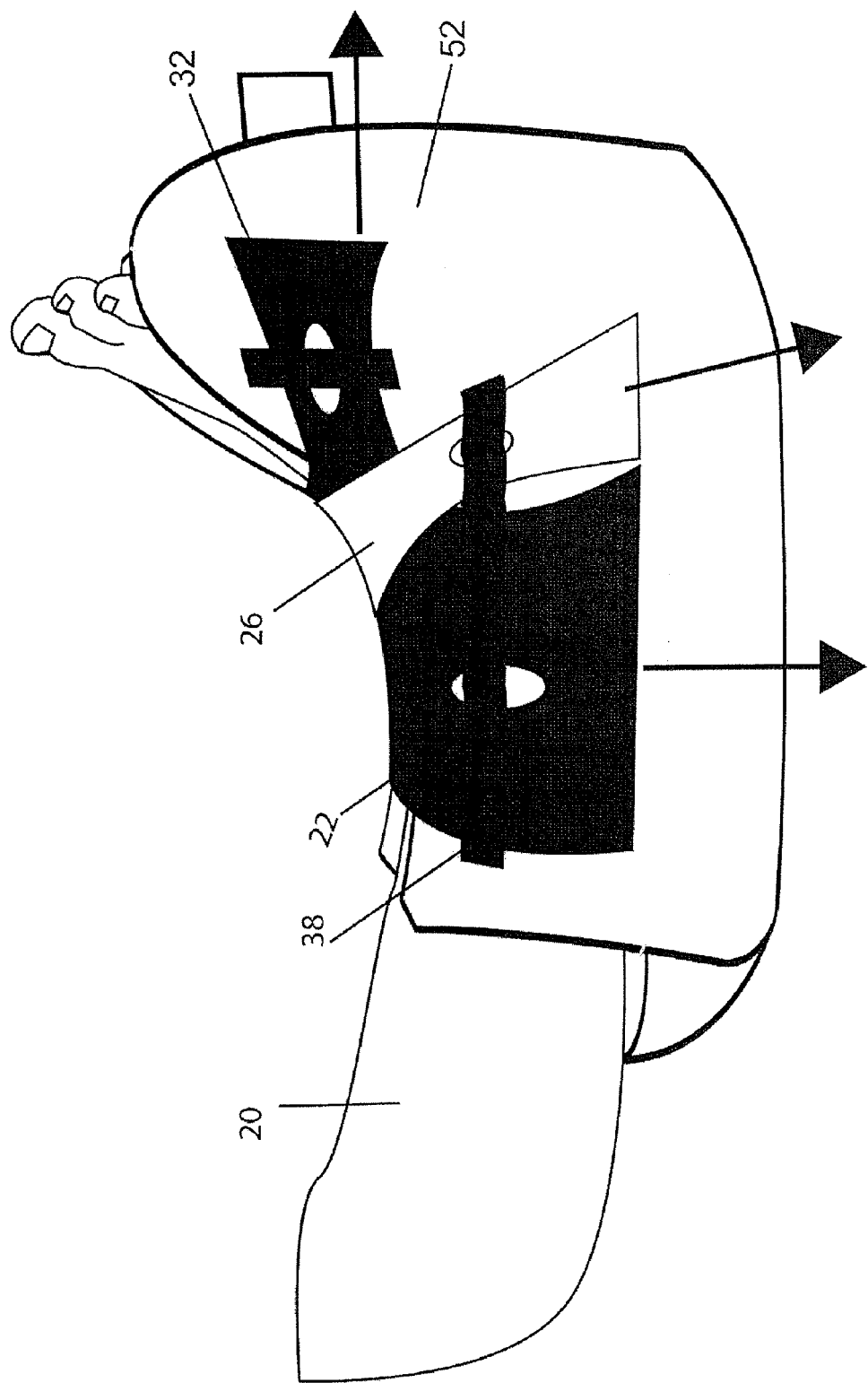
FIG. 17 is a side elevational illustration of the final step of donning the cushioning boot of FIG. 15.

A unique feature of the cushioning boot 10 is that, due to the complete removability of the panels 22 through 26, the cushioning boot 10 can be packaged in a ready-to-don fashion. That is, it can be packaged so that the user can remove it from the packaging, apply it to the patient, and then readily fasten it to the patient without having to disturb the patient or turn the patient to an uncomfortable position. To this end and as shown in FIGS. 15-17, it is preferred that the cushioning boot 10 is packaged inside out. That is, with the interior surface 50 out and with the exterior surface 52 turned inwardly, and the panels 22 through 28 at least being partially unattached to the exterior surface 52. To protect the hook portions 38, 42 and 48 from premature connection and to avoid tangling, those hook portions not in place can be covered with temporary protective covers, such as portable and disposable loop portions 84 that can be discarded when the cushioning boot 10 is deployed.

One of the advantages of the structure of the cushioning boot 10 is that the interior surface 50, where it contacts the patient's leg and foot, is smooth and not wrinkled so as to not irritate the patient when worn for long periods of time. By packaging the cushioning boot 10 inside out for deployment, that helps prevents wrinkles in the interior surface 50 (which is the temporary exterior surface when packaged inside out).

ACHIEVEMENTS

The panels 22 through 26 provide several unique features. Because large panels are used rather than rigid and narrow straps as in the past, the panels moderate pressure across leg tissue. The second panel portion 24 grips a person's foot about the arch, having a significant effect in keeping the boot 10 in place on the leg 20. The combination of the panel portions 22 and 24 helps prevent foot drop. The third panel 26 provides additional force and helps seat the leg 20 properly in place. Because the panels 22 through 26 are made of a stretchable material such as spandex or the like, various amounts of closure force can be provided, and even with fairly high force, because of the sizes of the panels 22 through 26, the force is adequately spread to avoid any pressure points.

As explained above, the padding 16 filling the cushioning boot 10 is intended to give it a pillow-like feel. Not only does the thick padding provide comfort, but it also helps properly orient the leg 20 within the boot 10. The padding 16 will self level and contours to the shape of the person's leg to provide uniformity of support.

The cushioning boot 10' more robustly orients a person's leg within the boot 10'. With the leg engaging portion 12' being formed into at least two partial tubes by means of the stitching 66, and with the tubular portions 72 and 74 of the foot engaging portion 14' being formed with the stitching 76, the person's leg and foot are properly oriented centrally within the cushioning boot 10', while comfort is not compromised because the second padded portion 62, although not as dense as the first padded portion 60, overlies the first padded portion for proper leg support and comfort.

With the exterior surface 52 having a low coefficient of friction and the interior surface 50 having a high coefficient of friction, a large frictional difference is provided. The high coefficient of friction of the interior surface 50 holds the leg 20 in place, while the low friction exterior surface 52 allows the leg, in the cushioning boot 10, to be readily moved. The combination of the low friction exterior surface 52 and high friction interior surface 50 combine to keep the leg 20 protected from pressure due to friction and sheer when the leg is moved, and also help prevent improper positioning of the leg 20 within the boot 10, which can lead to skin damage from misalignment of the boot 10 or skin exposure to bed surfaces.

Various changes can be made to the invention without departing from the spirit thereof or scope of the following claims.

What is claimed is:

1. A cushioning boot, comprising:
   a. a leg engaging portion and a foot engaging portion, and having a leg-accepting aperture extending along a front side of said boot, and
   b. said leg engaging portion comprising a leg orienting section and a leg cushioning section, said leg cushioning section being positioned toward said leg-accepting aperture and at least partially extending over said leg orienting section, and said leg orienting section comprising a pair of elongated, padded tubes joined at the center of the leg engaging portion and extending in a longitudinal direction substantially from a heel aperture proximate said foot engaging portion to a distal leg opening.

2. The cushioning boot according to claim 1, in which said leg cushioning section comprises a padding overlying said tubes.

3. The cushioning boot according to claim 1, in which said foot engaging portion is padded and includes a foot orientation section with a foot centering portion configured to center a foot.

4. The cushioning boot according to claim 3, in which said foot centering portion comprises a furrow extending longitudinally in said foot engaging portion.

5. A cushioning boot, comprising:
   a. a leg engaging portion and a foot engaging portion, and having a leg-accepting aperture extending along a front side of said boot,
   b. said leg engaging portion comprising a pair of padded, elongated tubes abutting one another and extending in a longitudinal direction substantially from a heel portion of said boot to a distal leg opening, and
   c. said foot engaging portion including a foot orientation section.

6. The cushioning boot according to claim 5, in which said foot orientation section comprises a furrow extending longitudinally in said foot engaging portion.

7. The cushioning boot according to claim 5, including a padding overlying said tubes.

8. The cushioning boot according to claim 5, in which said leg engaging portion comprises a leg orienting section and a leg cushioning section, said leg cushioning section being positioned toward said leg-accepting aperture and at least partially extending over said leg orienting section.

9. The cushioning boot according to claim 8, in which said leg orienting section comprises said pair of elongated, padded tubes.

10. A foot cushioning boot, comprising
   a. a leg engaging portion and a foot engaging portion,
   b. a pair of elongated tubes in said leg engaging portion, said tubes being substantially adjacent one another and extending in a longitudinal direction substantially from a heel aperture proximate said foot engaging portion to a distal leg opening, said tubes being filled with a padding having a first density,
   c. a padded portion overlying said tubes, said padded portion being filled with a padding having a second density, and
   d. said second density being lower than said first density.

11. The foot cushioning boot according to claim 10, including a stretchable, adjustable closure panel secured to said boot.

12. The foot cushioning boot according to claim 11, in which said closure panel is removable, and including a first portion of said panel extending substantially along said leg engaging portion.

13. The foot cushioning boot according to claim 12, including a second portion of said panel extending along a part of said foot engaging portion.

14. The cushioning boot according to claim 13, including a third stretchable, adjustable closure panel extending between and at least partly overlapping said first and second portions of said closure panel.

15. The cushioning boot according to claim 10, in which at least said leg engaging portion has an exterior surface having a low coefficient of friction and at least said leg engaging portion has an interior surface having a high coefficient of friction.

* * * * *